(12) United States Patent
Bryan

(10) Patent No.: US 9,549,904 B2
(45) Date of Patent: Jan. 24, 2017

(54) METHOD OF DESTROYING BACTERIAL BIOFILM USING STERILE INTRAVENOUS OR INTRACAVERNOUS GLYCERIN

(71) Applicant: Thomas Bryan, Merced, CA (US)

(72) Inventor: Thomas Bryan, Merced, CA (US)

( * ) Notice: Subject to any disclaimer, the term of this patent is extended or adjusted under 35 U.S.C. 154(b) by 553 days.

(21) Appl. No.: 13/912,060

(22) Filed: Jun. 6, 2013

(65) Prior Publication Data

US 2014/0018438 A1 Jan. 16, 2014

Related U.S. Application Data

(60) Provisional application No. 61/656,478, filed on Jun. 6, 2012.

(51) Int. Cl.

| | |
|---|---|
| *A61K 31/047* | (2006.01) |
| *A61K 9/19* | (2006.01) |
| *A61K 31/195* | (2006.01) |
| *A61K 31/198* | (2006.01) |
| *A61K 31/401* | (2006.01) |
| *A61K 31/405* | (2006.01) |
| *A61K 31/4172* | (2006.01) |
| *A61K 9/00* | (2006.01) |

(52) U.S. Cl.
CPC .......... *A61K 31/047* (2013.01); *A61K 9/0019* (2013.01); *A61K 31/195* (2013.01); *A61K 31/198* (2013.01); *A61K 31/401* (2013.01); *A61K 31/405* (2013.01); *A61K 31/4172* (2013.01)

(58) Field of Classification Search
CPC A61K 2300/00; A61K 31/047; A61K 31/195; A61K 31/198; A61K 31/401; A61K 31/405; A61K 31/4172; A61K 9/0019
See application file for complete search history.

(56) References Cited

U.S. PATENT DOCUMENTS

| | | |
|---|---|---|
| 5,711,937 A | 1/1998 | Nisjida et al. |
| 7,906,544 B2 | 3/2011 | Melander et al. |
| 8,241,611 B2 | 8/2012 | Dashper et al. |
| 8,420,673 B2 | 4/2013 | Pasteris et al. |
| 8,425,932 B2 | 4/2013 | Wryer et al. |
| 2011/0046041 A1 | 2/2011 | Neesham-Grenon et al. |
| 2011/0236453 A1 | 9/2011 | Stensen et al. |
| 2012/0315260 A1 | 12/2012 | Ivanova et al. |
| 2013/0059096 A1 | 3/2013 | Losick et al. |
| 2013/0123319 A1 | 5/2013 | Bryan |
| 2014/0018438 A1 | 1/2014 | Bryan |

FOREIGN PATENT DOCUMENTS

| | | | |
|---|---|---|---|
| EP | 2521542 A1 | 11/2012 | |
| WO | WO-2011/085326 A1 | 7/2011 | |
| WO | WO 2011085326 A1 * | 7/2011 | ........... A61K 31/198 |

OTHER PUBLICATIONS

Fitzpatrick et al., "Evidence for icaADBC-Independent Biofilm Development Mechanism in Methicillin-Resistant Staphylococcus aureus Clinical Isolates," Journal of Clinical Microbiology, 2005; 34(4): pp. 1973-1976.*
Helms et al., "Natural Treatment of Chronic Rhinosinusitis", Alternative Medicine Review, 2005, vol. 11, No. 9, pp. 196-207.

* cited by examiner

*Primary Examiner* — Sreeni Padmanabhan
*Assistant Examiner* — Jody Karol
(74) *Attorney, Agent, or Firm* — McCarter & English, LLP

(57) ABSTRACT

Disclosed is a method of preventing or inhibiting biofilm formation by a population of bacteria comprising the administration of a sterile intravenous normal saline solution containing glycerin and amino acids. In some embodiments, the concentration of glycerin in the normal saline solution is approximately 3%. In some embodiments, the concentration of amino acids in the normal saline solution is approximately 3%. In some embodiments, the intravenous solution is administered for 48 hours at 80 cc/hour. In some embodiments, the solution is infused via intracavernous administration into an infected body cavity.

19 Claims, No Drawings

METHOD OF DESTROYING BACTERIAL BIOFILM USING STERILE INTRAVENOUS OR INTRACAVERNOUS GLYCERIN

CROSS-REFERENCE TO RELATED APPLICATION

This application claims the benefit of priority of U.S. Provisional Patent Application 61/656478 filed Jun. 6, 2012 and titled "USE OF GLYCERINE IN TREATING BIOFILMS IN HUMANS AND ANIMALS," the disclosure of which is incorporated by reference.

BACKGROUND OF THE INVENTION

Field of Invention

This invention pertains to the use of sterile intravenous or intracavernous glycerin solutions to treat biofilms that infect humans and animals.

Description of Related Art

A biofilm occurs when bacteria stick to each other on a surface. These adherent cells are frequently embedded within a self-producing matrix of extra cellular polymeric substance. Biofilms are also referred to as slime. The polymeric conglomeration is generally composed of extra-cellular DNA, proteins and polysaccharides. Initially the biofilm is weak and adhesion is by van der Waals forces. Later, the bacteria form cell adhesion structures such as pili. Once colonization has begun the biofilm grows through a combination of cell division and recruitment.

The development of biofilm may allow for an aggregated cell colony to be increasingly antibiotic resistant. Bacteria from the biofilm can disperse which causes the spread and colonization of new surfaces. The matrix protects the bacteria within it and facilitates communication among them through biochemical signals. Biofilm has been implicated in such problems as urinary tract infections, endocarditis, cystic fibrosis and infections of prosthesis and heart valve. Invariably the only recourse for treating prosthetics such as mechanical heart valve is to have them replaced. Biofilms are present on the removed tissue of 80% of patients undergoing surgery for chronic sinusitis.

In the 1980's Danish pioneers first connected biofilms with human disease and then antibiotic resistant infections. They discovered that once these biofilm infections had begun they are difficult to get rid of in the body. The immune system can mop up free-floating bacteria in the blood but reaching bacteria in biofilms is difficult.

Even if an antibiotic reaches a biofilm, a large portion of the bacteria would be insensitive to the specific antibiotic as bacteria in a biofilm occupied a spectrum of physiological state from rapid growing to dormant. The dormant bacteria are not vulnerable to the antibiotic. Later, these dormant bacteria can quickly renew the biofilm. Low oxygen concentration in the biofilm also protects the bacteria from some antibiotics.

The CDC claims that 65% of bacterial infections that are treated by physicians develop biofilm. Biofilm have been implicated in chronic infections. Most notable among them is *staphylococcus aureus* especially the methicillin resistant variety, *staphylococcus epidermis* and *pseudomonas aeruginosa*. Topical glycerin can treat biofilm in the mouth such as halitosis.

A 66 year old female developed cellulitis and an open ulcer on her leg. This was treated by oral antibiotics and was also treated at an outpatient wound care center. When the outpatient care was not successful she was admitted to the hospital for intravenous antibiotics. After 3 weeks there was no sign of improvement and the ulcer was enlarging. At this stage the ulcer measured 3 cm by 1½ cm in size and there was surrounding redness suggestive of inflammation. She was then given intravenous glycerin. The intravenous glycerin was given as a solution of 3% glycerin and 3% amino acids. This is currently the only commercially available source of intravenous glycerin. She was given the infusion at a rate of 80 cubic centimeters (cc) per hour. At the end of 48 hours there was evidence of healing in the ulcer. During these 48 hours she was continued on intravenous antibiotics. After 72 hours the patient was discharged home on oral antibiotics. When she was re-examined 3 weeks later there was no evidence of the ulcer and the surrounding inflammation that was caused by cellulitis had totally cleared. Ulcers such as this patient had develop bacterial biofilm and can have increased resistance to antibiotics that at times cause the antibiotics to be ineffective.

SUMMARY OF THE INVENTION

A method is disclosed comprising the administration of intravenous normal saline solution containing glycerin and amino acids to prevent or inhibit internal biofilm formation by bacteria.

In some embodiments, the concentration of glycerin in the normal saline solution is approximately 3%.

In some embodiments, the concentration of amino acids in the normal saline solution is approximately 3%.

In some embodiments, the intravenous solution is administered for 48 hours at 80 cc/hour.

In some embodiments, the normal saline solution comprising a certain percentage concentration by volume of glycerin and a certain percentage by volume of an amino acid solution is infused into an infected body cavity.

In some embodiments, the bacterial infection comprises methicillin resistant *staphylococcus aureus*.

In some embodiments, the bacterial infection comprises *staphylococcus epidermis*.

In some embodiments, the bacterial infection comprises *pseudomonas aeruginosa*.

In some embodiments, the infected body cavity is a pleural cavity.

In some embodiments, the infected body cavity is a peritoneal cavity.

In some embodiments, approximately 500 cc of the normal saline solution comprising a certain percentage concentration by volume of glycerin and a certain percentage by volume of an amino acid solution is infused into an infected body cavity.

In some embodiments, greater than 500 cc of the normal saline solution comprising a certain percentage concentration by volume of glycerin and a certain percentage by volume of an amino acid solution is infused into an infected body cavity.

Also disclosed is a method of optimizing therapeutic efficacy for treatment of a bacterial infection within a body cavity comprising administering a normal saline solution comprising a certain percentage concentration by volume of glycerin and a certain percentage by volume of an amino acid solution.

DETAILED DESCRIPTION OF THE INVENTION

Glycerin is a simple polyol compound. Tons of it is produced annually in the United States and Europe. It is made from animal fats and vegetable oils. Only one company in the United States makes a product that is sterile and used for intravenous administration. It has been used since 1976 as a non-glycemic source of carbohydrates as a source of nutrition in patients who are unable to process food via the gastrointestinal tract. It is remarkable for its safety profile and is free of allergic reactions. It is generally infused at a 3% concentration at a rate of 80-100 milliliters per hour. Those with heart failure and kidney failure may need a slower rate of infusion. As in the case outlined here it can diffuse a bacterial biofilm.

Glycerin can assist antibiotics and the immune system in conquering bacteria biofilm. In this capacity it can reduce the ever-occurring resistance of bacteria to antibiotics. Cavity spaces such as the pleural cavity and the peritoneal cavity can develop infections with biofilms. Infusing these cavities with the 3% solution of Glycerin would help breakdown these biofilms. For example, half a liter of the solution would be infused into a pleural cavity. A greater amount could be infused into the peritoneal cavity.

Embodiments are directed to a method of treating a biofilm-associated infection in a subject comprising administering via an intravenous connection to the subject a normal saline solution comprising a certain percentage concentration by volume of glycerin and a certain percentage by volume of an amino acid solution.

In some embodiments, the concentration of glycerin in the normal saline solution is approximately 3%.

In some embodiments, the concentration of amino acids in the normal saline solution is approximately 3%.

In some embodiments, the intravenous solution is administered for 48 hours at 80 cc/hour.

In some embodiments, the normal saline solution comprising a certain percentage concentration by volume of glycerin and a certain percentage by volume of an amino acid solution is infused into an infected body cavity.

In some embodiments, the infusion occurs via intracavernous administration.

In some embodiments, the bacterial infection comprises methicillin resistant *staphylococcus aureus*.

In some embodiments, the bacterial infection comprises *staphylococcus epidermis*.

In some embodiments, the bacterial infection comprises *pseudomonas aeruginosa*.

In some embodiments, the infected body cavity is a pleural cavity.

In some embodiments, the infected body cavity is a peritoneal cavity.

A concentration higher than 3% of glycerin may be more effective.

Brand names include Procalamine from B. Braun Medical Inc.

ProcalAmine® (3% Amino Acid and 3% Glycerin Injection with Electrolytes) is a sterile, nonpyrogenic, moderately hypertonic intravenous injection containing crystalline amino acids, a nonprotein energy substrate and maintenance electrolytes.

A 1000 mL unit provides a total of 29 g of protein equivalent (4.6 g N) and 130 nonprotein calories.

All amino acids designated USP are the "L"-isomer with the exception of Glycine USP which does not have an isomer.

Table 1 provides the component weights per 100 mL.

TABLE 1

| Nonprotein energy source: | |
| --- | --- |
| Glycerin USP (glycerol) | 3.0 g |
| Essential amino acids | |
| Isoleucine USP | 0.21 g |
| Leucine USP | 0.27 g |
| Lysine (as Lysine Acetate USP 0.31 g) | 0.22 g |
| Methionine USP | 0.16 g |
| Phenylalanine USP | 0.17 g |
| Threonine USP | 0.12 g |
| Tryptophan USP | 0.046 g |
| Valine USP | 0.20 g |
| Nonessential amino acids | |
| Alanine USP | 0.21 g |
| Glycine USP | 0.42 g |
| Arginine USP | 0.29 g |
| Histidine USP | 0.085 g |
| Proline USP | 0.34 g |
| Serine USP | 0.18 g |
| Cysteine (as Cysteine HCl•H2O USP <0.020) | <0.014 g |
| Sodium Acetate•3H2O USP | 0.20 g |
| Magnesium Acetate•4H2O | 0.054 g |
| Calcium Acetate•H2O | 0.026 g |
| Sodium Chloride USP | 0.12 g |
| Potassium Chloride USP | 0.15 g |
| Phosphoric Acid NF | 0.041 g |
| Potassium Metabisulfite KF (as an antioxidant) | <0.05 g |
| Water for Injection USP | QS |
| pH adjusted with Glacial Acetic Acid USP pH | 6.8 (6.5-7.0) |
| Calculated Osmolarity | 735 mOsmol/liter |

These descriptions and drawings are embodiments and teachings of the present invention. All variations are within the spirit and scope of the present invention. This disclosure is not to be considered as limiting the present invention to only the embodiments illustrated.

What is claimed is:

1. A method of treating a biofilm-associated infection in a subject comprising administering to the subject, intravenously or intracavernously, a composition comprising approximately 3% L-amino acids by volume and approximately 3% glycerin by volume of saline solution.

2. The method of claim 1, wherein the composition is administered for 48 hours at 80 cc/hour by intravenous injection.

3. The method of claim 1, wherein the biofilm-associated infection comprises methicillin resistant *Staphylococcus aureus*.

4. The method of claim 1, wherein the biofilm-associated infection comprises *Staphylococcus epidermis*.

5. The method of claim 1, wherein the biofilm-associated infection comprises *Pseudomonas aeruginosa*.

6. A method of optimizing therapeutic efficacy for treatment of a bacterial infection comprising administering to a subject, intravenously or intracavernously, a composition comprising approximately 3% L-amino acids by volume and approximately 3% glycerin by volume in saline solution.

7. The method of claim 6, wherein the composition is administered via intravenous connection.

8. The method of claim 6, wherein the composition is infused via intracavernous administration.

9. The method of claim 6, wherein the bacterial infection comprises methicillin resistant *Staphylococcus aureus*.

10. The method of claim 6, wherein the bacterial infection comprises *Staphylococcus epidermis*.

11. The method of claim 6, wherein the bacterial infection comprises *Pseudomonas aeruginosa*.

12. The method of claim 6, the composition is administered intracavernously into a pleural cavity of the subject.

13. The method of claim 6, the composition is administered intracavernously into a peritoneal cavity of the subject.

14. The method of claim 6, wherein a volume of approximately 500 cc of the composition is infused intracavernously into an infected body cavity.

15. The method of claim 6, wherein a volume of greater approximately than 500 cc of the composition is infuse intracavernously into an infected body cavity.

16. The method of claim 1, wherein the composition is Procalamine®.

17. The method of claim 6, wherein the composition is Procalamine®.

18. The method of claim 1, wherein the composition is administered intravenously.

19. The method of claim 1, wherein the composition is administered intracavernously.

\* \* \* \* \*

UNITED STATES PATENT AND TRADEMARK OFFICE
CERTIFICATE OF CORRECTION

| | | |
|---|---|---|
| PATENT NO. | : 9,549,904 B2 | Page 1 of 1 |
| APPLICATION NO. | : 13/912060 | |
| DATED | : January 24, 2017 | |
| INVENTOR(S) | : Thomas Bryan | |

It is certified that error appears in the above-identified patent and that said Letters Patent is hereby corrected as shown below:

In the Claims

Column 5, Line 1, for the Claim referenced numeral "12", should read:
The method of claim 6, wherein the composition is administered intracavernously into a pleural cavity of the subject.

Column 5, Line 3, for the Claim referenced numeral "13", should read:
The method of claim 6, wherein the composition is administered intracavernously into a peritoneal cavity of the subject.

Column 5, Lines 12 and 14, for the Claims referenced numerals "16" and "17", the name should be changed to -ProcalAmine®-

Signed and Sealed this
Fourth Day of July, 2017

Joseph Matal
*Performing the Functions and Duties of the
Under Secretary of Commerce for Intellectual Property and
Director of the United States Patent and Trademark Office*